United States Patent [19]

Sinclair

[11] 4,134,169

[45] Jan. 16, 1979

[54] OSCILLATING POWER BRUSH

[76] Inventor: James A. Sinclair, 303 Present Rd., Missouri City, Tex. 77459

[21] Appl. No.: 829,903

[22] Filed: Sep. 1, 1977

Related U.S. Application Data

[63] Continuation-in-part of Ser. No. 710,273, Jul. 30, 1976, abandoned.

[51] Int. Cl.² ............................................. A46B 13/02
[52] U.S. Cl. .................................... 15/22 R; 74/87; 128/37; 128/62 A
[58] Field of Search ................. 128/35, 36, 37, 62 A; 15/22 R, 22 A, 22 C; 310/81; 32/58; 74/61, 87

[56] References Cited

U.S. PATENT DOCUMENTS

| 816,365 | 3/1906 | Olson | 128/37 X |
|---|---|---|---|
| 1,082,285 | 12/1913 | Peterson | 128/37 |
| 1,267,833 | 5/1918 | Wilson | 128/37 |
| 3,183,538 | 5/1965 | Hubner | 128/36 X |
| 3,318,163 | 5/1967 | Matson | 128/37 X |
| 3,466,689 | 9/1969 | Aurelio et al. | 15/22 R |
| 3,507,599 | 4/1970 | Meszaros et al. | 128/37 X |

*Primary Examiner*—Edward L. Roberts
*Attorney, Agent, or Firm*—Roy H. Smith, Jr.

[57] ABSTRACT

A brush is rigidly attached to one end of a housing having a handle at the other end and, between the ends, a cylindrical opening supporting a rotor whose center of mass is displaced laterally from the axis of rotation. As the rotor turns, it exerts an unbalanced centrifugal force on the housing, causing it to oscillate. The rotor is preferably a single metal roller gyrating or rotating about the axis of the cylindrical opening, and it may be rotated by a tangential stream of fluid, e.g., water at utility district pressure. The rotor body may be solid or a hollow member filled with a heavy liquid such as mercury, and it is so supported that during rotation its outer peripheral surface approaches but does not touch the borewall of the opening in which it operates.

10 Claims, 10 Drawing Figures

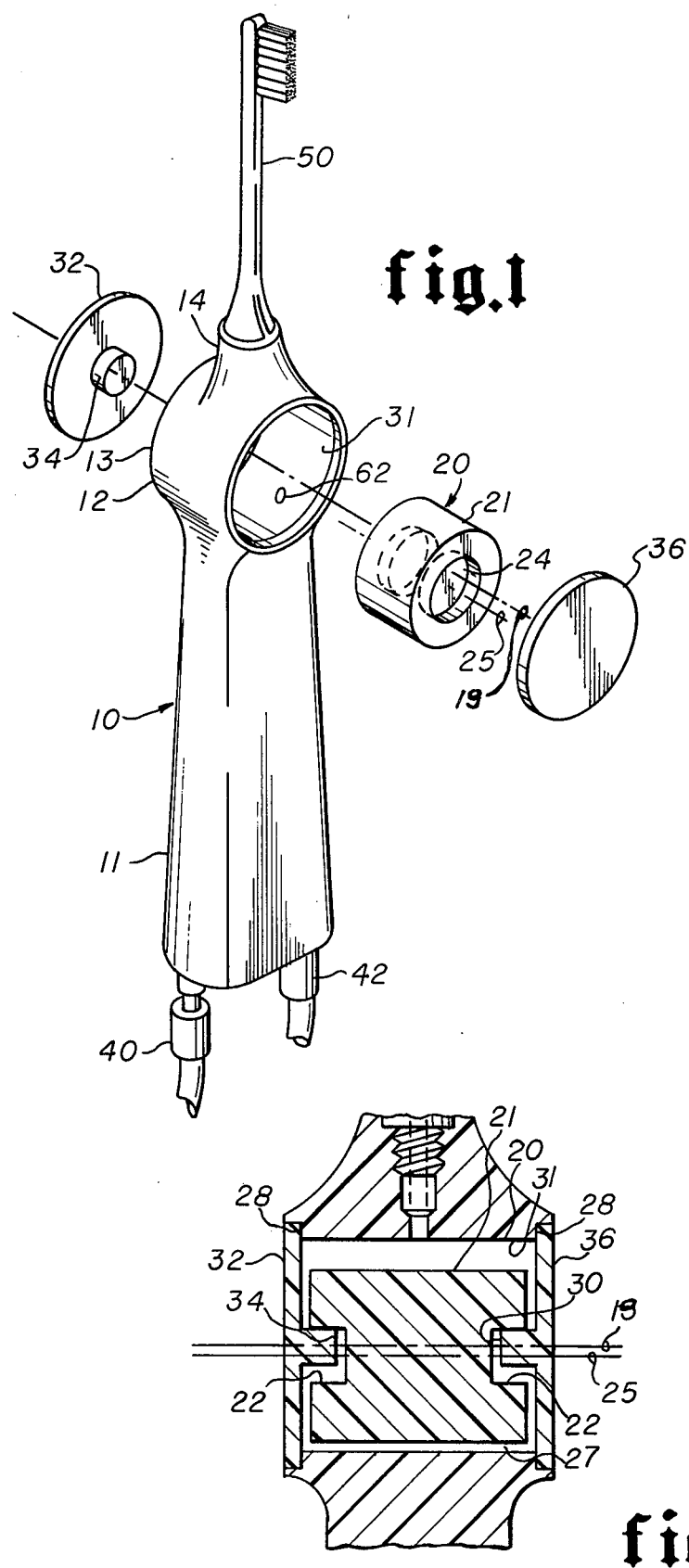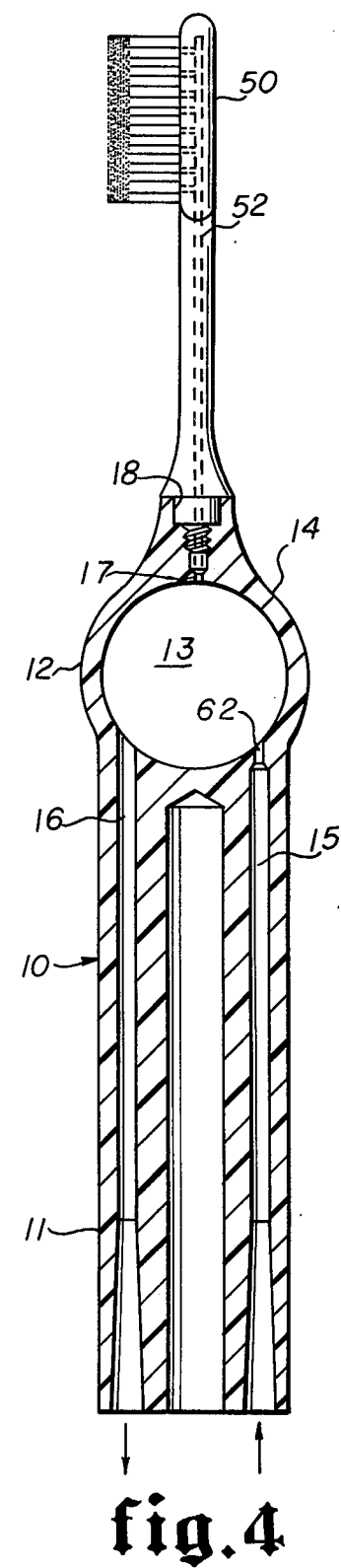
fig.1
fig.2
fig.4

OSCILLATING POWER BRUSH

RELATIONSHIP TO OTHER APPLICATIONS

The present application is a continuation-in-part of an earlier patent application of the same inventor, partially diminished and containing some new matter. Such earlier application is identified as Ser. No. 710,273, and was filed on July 30, 1976. It has now been abandoned.

FIELD OF INVENTION

The present invention lies broadly in the field of brushes and vibrators, and more particulary in the arena of power brushes. The utilization illustrated and described herein is that of a toothbrush, but the structure and operating concept are applicable to brushes generally.

PRIOR ART

Prior art power brushes are characterized mainly by rotors which rotate about fixed axes, the rotor developing centrifugal force on the housing by virtue of its unbalanced distribution of mass. Thus in the massage device of Olson, U.S. Pat. No. 816,365, the rotor simply rotates about a fixed shaft and includes an unbalancing weight "1" or "1'." In the toothbrush of Hubner, U.S. Pat. No. 3,183,538, a rotating disc 9 contains a multiplicity of imbalancing weights 13 and rotates with its fixed shaft 10. Likewise the toothbrush of Aurelio, U.S. Pat. No. 3,466,689, utilizes a rotor 48 provided with eccentrically mounted weights 56, and the same is true of the Meszaros toothbrush, U.S. Pat. No. 3,507,599. It is important to observe that in the operation of each of these four devices every point on the rotor describes a circle about the rotor's axis of rotation, and that all such circles are concentric.

The vibratory device of Peterson, U.S. Pat. No. 1,082,285 is of a different nature. Peterson discloses the use of a ball which is rolled around a circular raceway under the influence of a tangential stream of motive fluid. The ball has a diameter somewhat less than half that of the raceway and rolls directly on the raceway, and of course there is wear between the two and a good bit of clatter.

Another item of distinction lies in the relative dispositions of the axes of the bristles of the brush and the axis of rotation of the rotary member. A brush requires motion only in directions parallel to the surface being cleaned, i.e., in directions perpendicular to the bristles. On the other hand, an imbalanced rotor can cause centrifugal effects and brush movements only in planes normal to its axis of rotation. These two considerations dictate that the axis of rotation should be disposed to be parallel to the bristles of the brush, whereas in fact in the prior art brushes just described the axis of rotation is perpendicular to the bristles of the brush. This will cause an undesirable component of motion parallel to the bristles, i.e., in a toothbrush, a hammering on the teeth.

SHORT STATEMENT OF THE INVENTION

The principal object of the present invention is a power brush operating on the principle that a rotating assembly having a center of mass offset from the axis of rotation delivers an unbalanced centrifugal force to the housing or other member restraining the rotating assembly to its prescribed course.

Another object is to provide a power brush in which the housing of the brush is deliberately oscillated by the action of a dynamically imbalanced mass rotating within the housing, and a bristle-bearing member is attached to the housing and oscillates with it.

A further object is to provide a power toothbrush oscillating in the manner recommended by the dental profession, with strokes of small amplitude; a preferred motion is an eliptical orbit, with the major axis parallel to the axis of the teeth and the minor axis across the teeth, respectfully normal and parallel to the elongated handle of the usual brush, held in the typical horizontal position. Kindred objects for such toothbrushes are a high frequency of oscillation to minimize the time required for the requisite number of strokes, to encourage teeth brushing by making such brushes simple and pleasant to use, to make them free of sliding parts and rotating seals, and to make them easily rinsed and submerged without damage.

Other objects are to provide such a power brush which efficiently converts energy from an external source to power strokes of a bristle-bearing member, which minimize sliding friction and rotating seals, which can operate well with water power, electric power, or other sources of power, which utilizes efficient combinations of materials in its various parts, which can be utilized to operate auxiliary devices such as water jets and oscillating tooth picks, which can be safely operated by untrained persons with little or no hazard, and which can be fabricted and marketed at a relatively low cost.

The inventive concept is primarily that of using a dynamically imbalanced rotor or rotating assembly so that the resulting imbalanced centrifugal force continuously delivers rotating impacts to the housing of a power brush containing the rotor and having a bristle member secured to it. Since in many applications the housing will also be used as a handle, and the user's hand tends to damp the oscillation of the housing, it is an important part of the invention to provide a gripping portion or handle disposed away from the vibrator and brush sections of the housing, the portions containing the rotor opening and the brush socket. It is also a part of the inventive concept to reduce the mass of the housing material between the vibrator section and the point at which the brush is mounted, to increase the amplitude of vibration of the brush-mounting section, which in turn will cause larger amplitudes of vibration of the toothbrush in planes parallel to the teeth. Further refinement of the basic concept involves maximizing the relative masses of the driving members relative to the driven members, as by making parts of the rotating assembly of heavy metal while making the housing and bristle member of relatively light but tough plastics. Speed control is exploited to control both frequency of oscillation and centrifugal force ($MV^2/r$), whenever possible, particularly in selecting the motor of an electric drive, but is essentially fixed when water power is used.

The structure of the power brushes of the present invention is controlled by the geometry of the rotary mass. Through both analysis and by trial and error the present inventor has discovered that, in using a stream of pressurized fluid as his motive source, a very good if not optimum configuration is a single roller having a diameter of ⅔ of the diameter of the raceway it travels around under the influence of the fluid stream. It should be noted here that a single roller or ball will travel around a circular raceway having a vertical disposition (horizontal axis of rotation), under the influence of a relatively low momentum stream, without the need for any assistance when the roller passes above its center and there experiences maximum gravitational pull.

There are disadvantages to the use of a roller which rolls about a circular raceway defined by the inner surface of a cylindrical cavity, not the least of which is chattering. In addition, when caused to rotate by a tangentially introduced stream of fluid the roller spins about its own axis in a direction opposed to the vortex velocity of the fluid stream, reducing the efficiency of the system. There are also wear problems, and for all these reasons it is a considerable improvement to let the roller approach the bore of the cavity but avoid actual contact, and transfer the centrifugal force developed during rotation to the housing through a shaft. This can be done by providing an axial bore down the center of the roller and mounting it on a non-rotating full length shaft or bearing pin, the bearing pin having an outside diameter which is smaller than the bore of the roller so that the roller rolls on the pin in the manner of a "Hula Hoop." This considerably reduces the noise level, causes the roller to spin in the same direction as the vortex, and reduces the wear problem.

Since a full length axial opening through the roller causes a considerable reduction in its mass and thus in its developed centrifugal force, it is a further improvement to make the bulk of the roller solid and provide only a partial axial opening from each of its axial extremities, mounting it so that the pair of opposed openings surround a pair of stub shafts secured to the housing. Of course, the stub shafts can be made integral with the roller and the oversize openings provided in the housing to accomplish the same purpose. In an alternate embodiment, the stub shafts are secured off-center to the body of the roller and are mounted in housing openings of the same size; in this form of the invention there is no "Hula Hoop" motion, but one of the stub shafts may be extended through the housing for connection to an external source of rotary power.

An additional improvement is to make the body of the roller hollow and fill it, or partially fill it, with a heavy liquid such as mercury. A partial filling, while it reduces the mass of the rotary assembly in comparison with a complete filling, causes an increase in the radius of gyration because the heavy liquid is concentrated at the outside of the rotating roller. (It should be noted that the centrifugal force of the system, $MV^2/R$, can also be expressed as $Mw^2R$ because V, the instantaneous linear velocity of the centroid of the rotating assembly, is equal to $wR$, where $w$ is the angular velocity of the system. Since $w$ is externally determined, the centrifugal force is directly proportional to the product of the mass of the roller and the radius of its centroid. Any change in mass which also changes the location of its centroid, as in a partial liquid filling, must be examined specifically to see if an improvement results.

Finally, the present invention comprehends a "Hula Hoop" type of structure utilizing an elliptical bearing pin or pair of stub shafts. This has the advantage of affording a measure of control over the relative amplitudes of the developed centrifugal forces along the major and minor axes of the elliptical bearing pin. Such bearing pin may be moved from one orientation to another to take full advantage of this versatility.

BRIEF DESCRIPTION OF THE DRAWINGS FIGURES

In the accompanying drawing:

FIG. 1 is an exploded view of a power brush of the present invention employed as a tooth brush.

FIG. 2 is an enlarged axial section of the vibrator section of the power brush shown in FIG. 1.

FIG. 4 is a sectional view of the housing and brush members of FIG. 1, modified to provide a diversionary channel so that part of the water may be utilized in the bristles of a tooth brush.

DETAILED DESCRIPTION OF THE DRAWING FIGURES

Figure 3:
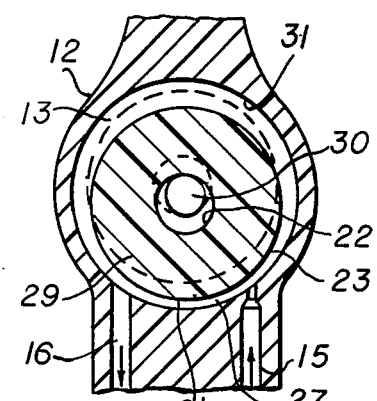
FIG. 3 is a cross section of the same vibrator section, showing the relationship of roller, bearing pin and housing.

The present invention will be more readily understood by reference to the drawing, read together with the following:

The exploded view of FIG. 1 and the sections of FIGS. 2 and 3 portray a preferred embodiment of the present invention, one in which the power brush is specifically a toothbrush. The principal components are housing member 10 and rotating assembly 20, together with the closure caps 32 and 36 and stub shafts 34 and 30 respectively secured to caps 32 and 36. To supply water or other motive fluid to the brush, an inlet conduit 40 and an exit conduit 42 are connected to the lower end of housing 10, in fluid flow relationship with a pair of internal longitudinal passageways 15 and 16, (see FIGS. 3 and 4). Brush 50 is rigidly secured to the housing 10 by any convenient means, preferably in a removable fashion for quick replacement. Both the brush and the housing are preferably made of a tough but lightweight plastic material, so that their masses are small compared with that of the rotating assembly 20, preferably made of a relatively heavy metal such as steel or even lead.

Housing 10 is divided into three principal sections, a lower section 11 which serves as a handle, a rotor section 12 containing the generally cylindrical cavity 13 which receives the rotating assembly 20, and an upper section 14 which supports the brush 50. Note that the housing is quite thin on either side of rotor section 12, to encourage high amplitude vibrations in the lateral direction. As shown in FIG. 4, which adds an optional diversionary channel 17 branching off from imput passageway 15 to direct fluid into the toothbrush socket 18, and up the toothbrush passageway 52, the lower end 11 is adequate for holding purposes and is spatially isolated from the upper end 14 which connects the rotor section 12 to brush 50. This is an important feature of the invention, as it is desirable to cause section 14 and brush 50 to oscillate albeit with a smaller amplitude axially than in the lateral direction. With handle end 11 isolated, the user in normal use will not damp out the oscillations in section 14 by gripping the same.

The generally cylindrical transverse opening 13 is provided with counterbores 28 to receive the opposed pair of end closures 32 and 36. These closure members are sealingly secured in place by virtue of a tight fit, together with exterior welding at their circumferences.

The rotating assembly 20 of the illustrated preferred embodiment consists entirely of the rotor 21, having the pair of opposed end openings 24 to loosely receive the stub shafts 30 and 34 extending toward one another from closure caps 36 and 32. It should be noted that rotor 21 by itself is statically balanced, as the material thereof is symmetric in an axis of revolution coincident with the axis 25 of central opening 24. The center of mass of rotor 21 lies on the axis of rotation 25, which is another way of saying that rotor 21 is statically balanced, and the rotor by itself could not be rotated about its own axis 25 to produce the desired oscillations.

Since the illustrated rotor 21 is statically balanced, the only means by which it can be used to produce vibrations is by imbalancing it dynamically. Basically, the rotor is caused to rotate about an axis 19 which is displaced laterally from its own axis of symmetry 25. Another way of expressing the same method of operation is to say that in operation the center of mass or centroid of the rotor rotates about an axis of rotation and is spaced from such axis at a radius called the radius of gyration. Since there is a radius of gyration, the rotating member 21 exerts 21 exerts a centrifugal force, $CF = Mw^2R$, on the housing as the rotor 21 rolls about the opening 13 with its interior surfaces 22 rolling over the circumference of bearing pins 30 and 34. This can be seen to better advantage in FIGS. 2 and 3, from which it is evident that the openings 22 have a larger diameter than that of the bearing pins. In these figures the rotor 21 is shown at rest, hanging free from a position in contact with the bearing pin at the top dead center position. As is evident in this figure, the outer surface 23 very nearly touches the borewall 31 of the main opening 13, but is separated therefrom by the small gap 27. In operation the fluid stream or vortex pushes against the roller and some fluid flows through the gap 27, rotating the roller on its own axis and at the same time causing it to roll around the bearing pin, in Hula Hoop fashion.

It can be shown that the optimum ratio of the diameter of roller 21 to a given diameter of opening 13 is $\frac{2}{3}$. With the diameter of surface 23 thus fixed, it is apparent that this surface will move upwardly from the rest position shown in solid lines in FIG. 3 to the opposite position shown in dashed lines a distance of $\frac{1}{3}$ the diameter of counterbore 31 (temporarily ignoring gap 27 for a rough calculation). Since the interior wall 22 must move through the same vertical distance, the diameter of wall 22 is thus fixed at $\frac{1}{3}$ the diameter of opening 13 plus the diameter of bearing pin 30. Some design choice remains as to the bearing pin, and once it is fixed, the thickness of the annular ring 29 between interior surface 22 and exterior surface 23 is determined. Thus if the opening 31 is of 3-inch diameter and surface 23 of rotor 21 is fixed at 2 inches, the diameter of pin 30 might be set at $\frac{1}{2}$ inch, making the diameter of interior surface 22 1$\frac{1}{2}$ inches and the thickness of annulus 29 $\frac{1}{4}$-inch.

Figure 5:
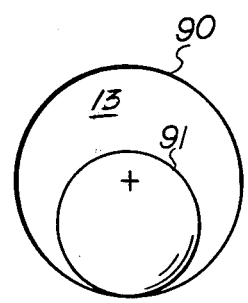
FIG. 5 is a schematic view of an embodiment wherein the entire rotating assembly is a single ball or roller, rolling in the indicated raceway.

FIG. 5 illustrates the range of the invention when the driver is to be a jet of fluid directed around a raceway such as 90, which represents the borewall through a vibrator housing. In this form of the invention no shaft or bearing pin is required, and the rotary assembly takes the form of a single ball or roller. As previously indicated, one of the best configurations discovered by the present inventor is a single ball or roller 91 having a diameter equal to about $\frac{2}{3}$ of the diameter of the raceway 90 around which it is driven.

FIG. 4 has been partially described above, in connection with FIG. 1. This sectional view shows the diversionary channel 17 which may be used to divert some of the incoming fluid through a similar channel 52 in toothbrush 50, thereby converting it to an irrigated brush. When no such irrigation is desired, an ordinary brush having no channel in it will prevent such flow, but diversionary channel 17 will still serve a useful purpose, specifically as a drainage channel after a period of time.

Figure 10:
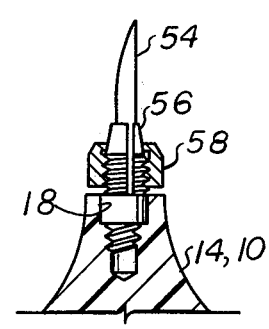
FIG. 10 is a section view of a housing of the invention supporting for vibration a tooth cleaning device similar to a toothpick.

FIG. 10 illustrates a use of the present power brushes to hold and vibrate a toothpick-like device 54 sold under the trademark "Stimudent." Such a device has a chisel type operating tip, but does not scratch teeth because it is made of balsa, a very soft wood. As shown, it is held in a collet 56 gripped by a chuck 58 and secured in the socket 18 of the brush end 14 of housing 10.

Figure 6:
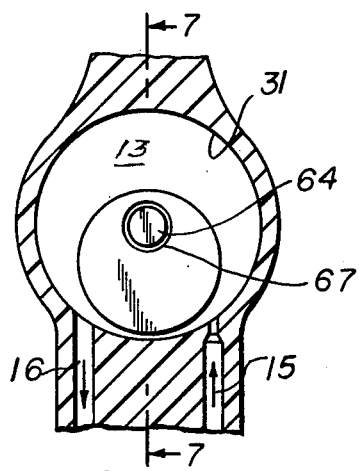
FIG. 6 is a cross section of a vibrator section using a solid rotor with a pair of eccentrically disposed integral stub shafts supporting in bearings of the same size.
Figure 7:
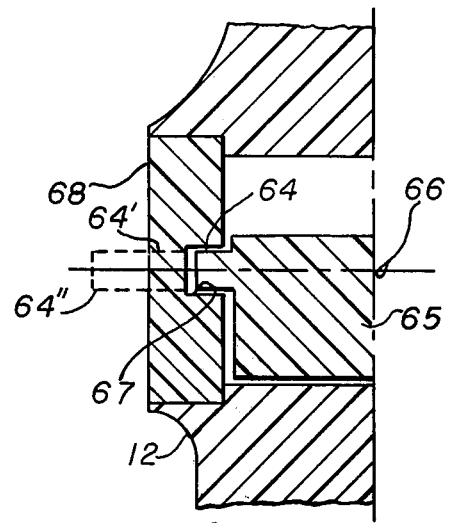
FIG. 7 is a longitudinal section of the FIG. 6 embodiment, as indicated by the sectioning lines and arrows marked "7—7" therein.

FIGS. 6 and 7 illustrate an alternate embodiment wherein the stub shafts 64 are made integral with a rotor 65 which is asymmetric with respect to such stub shafts. The pair of coaligned stub shafts 64, only one of which is shown in the half-section of FIG. 7, are centered on axis 66 of the housing 12 and extend into like size openings 67 in the end caps 68, where they are supported in common journal bearing relationship. In this form of the invention the entire rotary assembly simply rotates about axis 66, all points describing concentric circles. It has the advantage, however, that it can be rotated by an externally located rotary device as well as by a tangential stream of fluid. This can be accomplished, for instance, by extending the stub shafts 64 through end caps 68, as indicated at 64' and 64".

Figure 8:
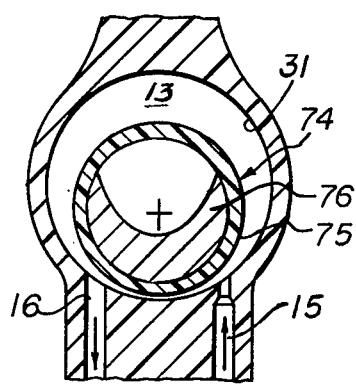
FIG. 8 is a cross similar of a vibrator section using a hollow rotor partially filled with a heavy liquid.

FIG. 8 illustrates a form of the invention in which the body of rotor 74 is a hollow shell 75 containing a filling or partial filling 76 of a heavy liquid such as mercury. In other respects the overall assembly may be like those described previously. It wil be evident in this form of the invention that the heavy liquid will be thrown to the outside as the rotor is rotated, shifting the center of mass outwardly and thus increasing the radius of gyration and the centrifugal force developed by the rotating assembly. With this form of the invention the rotor may be mounted in the housing using any of the mounting structures previously described.

Figure 9:
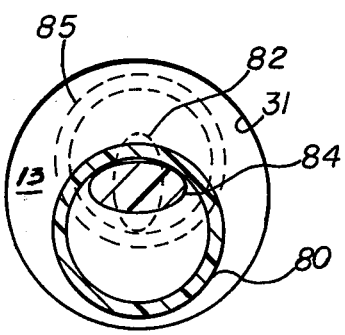
FIG. 9 is a cross section of a vibrator which includes an elliptical bearing pin.

Finally, the cross section of FIG. 9 illustrates a vibratory rotary assembly differing from those previously described only in the use of an elleptical bearing pin 84. In this FIG. 80 represents the rotor or rotor end in free position and 85 represents another position of the rotor, during rotation; the large circle represents the borewall of the rotor cavity in a vibrator housing. The rotor or rotor end 80 has the usual circular geometry, but during rotation the center of mass of the rotary assembly follows an elliptical trajectory 82 wherein the major and minor axes are rotated 90° degrees by comparison with the position of the bearing pin. It will be apparent that in the vertical position the centrifugal force is relatively large while along the horizontal axis the force is relatively small. The resulting vibrations will have similarly large and small amplitudes, thus providing some control over the resulting scrubbing action of the brush. In addition, the bearing pin or stub shaft 84 may be rotated 90° degrees from the position shown, thus giving another measure of control.

Now that specific embodiments have been described, it will be apparent that many other forms of the invention may be conceived by varying the details and arrangements disclosed, and it is to be understood that all such variations which achieve the same ends by equivalent or substantially similar means operating in substantially the same manner are within the spirit and scope of the invention. As one example, the rotary assembly may include various members which combine rotation with various other motions, e.g., like a barrel hoop rolling around a small diameter pipe. Since such variants are within the inventive concept, the invention should not be limited except by the following claims.

What is claimed is:

1. In a power brush, a vibrator section including
   A. a housing having a rotor opening therethrough defined by a borewall, said opening defining a pair of opposed ends and having a longitudinal axis, and cross sectional dimensions defined by said borewall,
   B. a pair of closure caps disposed at said opposed ends,
   C. a statically balanced rotor disposed in said opening, and
   D. shaft means and shaft journal means on said closure caps and rotor, the shaft means being on one of them and the journal means on the other, the shaft means extending longitudinally into the journal means and being laterally supported thereby,
   D1. said journal means being a number of bores having a larger diameter than said shaft means and permitting said rotor to rotate with its outer surface approaching said borewall of the rotor opening but not contacting the same, whereby said rotor may be thus rotated under the influence of a fluid stream directed tangentially into said rotor opening with said shaft means rolling over the bores of said journal bearing means.

2. The power brush vibrator section of claim 1 in which said said rotor is a solid cylinder and said bores of the journal means are formed concentrically on the rotor axis.

3. The power brush vibrator section of claim 2 in which there are a pair of said bores in the rotor from the opposed ends thereof, said bores being opposed and separated from one another, and said shaft means is a pair of opposed stub shafts supported by said closure caps.

4. The power brush vibrator section of claim 1 in which said rotor is a hollow shell at least partially filled with a heavy liquid.

5. The power brush vibrator section of claim 4 in which said liquid is mercury.

6. The power brush vibrator section of claim 1 in which said shaft means is of elliptical cross section and said bores of the journal means have a diameter larger than the length of the major axis of said elliptical shaft.

7. A power brush comprising a housing having a brush-mounting section at one end and a handle section at the other end, and
   a vibrator section disposed between said brush-mounting section and said handle section, said vibrator section including a cylindrical chamber formed in said housing, a rotor disposed in said chamber for planetary motion therein about the axis of said chamber, a pair of end caps closing said chamber and supporting the opposed ends of said rotor, and means for rotating said rotor about said chamber axis,
   each said end cap and the adjacent end of said rotor engaging one another in journal bearing fashion by means of a stub shaft on one member extending cantilever fashion into a blind bore in the other, the diameter of said bore being larger than the diameter of said stub shaft by an amount permitting the roller to rotate in planetary fashion with the surface of said bore in contact with the peripheral surface of the stub shaft but without contact between the outer surface of the roller and the borewall surface of said chamber.

8. The power brush of claim 7 wherein said rotating means comprises a first conduit in said handle section extending into said vibrator section for delivering a tangentially directed stream of fluid into said chamber adjacent the wall thereof, and a second conduit for carrying said fluid out of the brush.

9. The power brush of claim 7 in which said brush-mounting section is adapted to receive and hold the handle end of an L-shaped brush in which one leg of the L is the handle and the other leg is an array of bristles extending at right angles to the brush, and in which said cylindrical chamber is disposed so that its axis is parallel to said bristles, whereby in operation said bristles are vibrated in directions lying in planes perpendicular to their axial lengths.

10. A power brush comprising a housing which also serves as a handle and as a support for a work member such as a bristle-bearing member, together with a rotating assembly secured in a generally cylindrical cavity in said housing and means for connecting said rotating assembly to a source of rotary power, said rotating assembly being dynamically imbalanced with respect to the cylindrical axis of said cavity in that the center of mass of such assembly is disposed off-center from said axis, said rotating assembly comprising a center section which is statically balanced about a longitudinal axis and a pair of integral bearing pins which are eccentrically disposed with respect to such longitudinal axis, said bearing pins being received in journal bearing openings in the housing which are of the same cross-sectional dimensions as the bearing pins except for operational clearance.

* * * * *